(12) United States Patent
Elson et al.

(10) Patent No.: US 7,238,678 B2
(45) Date of Patent: *Jul. 3, 2007

(54) ADHESIVE N,O-CARBOXYMETHYLCHITOSAN COATINGS WHICH INHIBIT ATTACHMENT OF SUBSTRATE-DEPENDENT CELLS AND PROTEINS

(75) Inventors: Clive Elson, Halifax (CA); Timothy D. G. Lee, Halifax (CA)

(73) Assignee: Chitogenics, Inc., Chatham, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/103,354

(22) Filed: Apr. 11, 2005

(65) Prior Publication Data

US 2005/0244454 A1   Nov. 3, 2005

Related U.S. Application Data

(60) Division of application No. 10/672,072, filed on Sep. 25, 2003, now Pat. No. 6,894,035, which is a continuation-in-part of application No. 09/315,480, filed on May 20, 1999, now Pat. No. 6,645,947.

(51) Int. Cl.
*A61K 31/73* (2006.01)
*C12N 5/00* (2006.01)

(52) U.S. Cl. .................................. 514/55; 435/325
(58) Field of Classification Search .............. 514/55; 536/20; 435/41, 325
See application file for complete search history.

(56) References Cited

U.S. PATENT DOCUMENTS

| | | | | |
|---|---|---|---|---|
| 4,424,346 A | | 1/1984 | Hall et al. .................. 536/20 |
| 4,603,695 A | * | 8/1986 | Ikada et al. .................. 606/1 |
| 4,615,697 A | | 10/1986 | Robinson .................. 424/428 |
| 4,619,995 A | | 10/1986 | Hayes .................. 536/20 |
| 4,659,700 A | | 4/1987 | Jackson .................. 514/55 |
| 4,868,113 A | | 9/1989 | Jaye et al. .................. 435/69.4 |
| 4,886,787 A | | 12/1989 | De Belder et al. .................. 514/57 |
| RE33,375 E | | 10/1990 | Luck et al. .................. 514/2 |
| 4,978,332 A | | 12/1990 | Luck et al. .................. 604/19 |
| 5,080,893 A | | 1/1992 | Goldberg et al. .................. 514/57 |
| 5,093,319 A | | 3/1992 | Hingham et al. .................. 514/55 |
| 5,234,915 A | | 8/1993 | Mathur et al. .................. 215/57 |
| 5,412,084 A | | 5/1995 | Elson .................. 536/20 |
| 5,510,102 A | | 4/1996 | Cochrum .................. 424/78.08 |
| 5,578,661 A | * | 11/1996 | Fox et al. .................. 524/27 |
| 5,679,658 A | | 10/1997 | Elson .................. 514/55 |
| 5,840,777 A | * | 11/1998 | Eagles et al. .................. 521/82 |
| 5,851,461 A | * | 12/1998 | Bakis et al. .................. 264/50 |
| 5,888,988 A | * | 3/1999 | Elson .................. 514/55 |
| 5,948,401 A | | 9/1999 | Donabedian et al. .................. 424/78.04 |
| 6,030,635 A | * | 2/2000 | Gertzman et al. .................. 424/423 |
| 6,197,325 B1 | * | 3/2001 | MacPhee et al. .................. 424/426 |
| 6,224,794 B1 | * | 5/2001 | Amsden et al. .................. 264/4.1 |
| 6,645,947 B1 | * | 11/2003 | Elson et al. .................. 514/55 |
| 6,894,035 B2 | * | 5/2005 | Elson et al. .................. 514/55 |

FOREIGN PATENT DOCUMENTS

| | | |
|---|---|---|
| DE | 19604180 A1 * | 8/1997 |
| DE | 19724869 A1 * | 12/1998 |
| EP | 0312208 | 4/1989 |
| EP | 0368253 | 5/1990 |
| EP | 0637450 | 2/1995 |
| EP | 0650999 | 5/1995 |
| EP | 0665022 | 8/1995 |
| WO | WO 86/00912 A1 * | 2/1986 |
| WO | WO86/00912 A1 * | 2/1986 |
| WO | WO 87/07618 A1 * | 12/1987 |
| WO | WO87/07618 A1 * | 12/1987 |
| WO | WO 93/13137 A1 * | 7/1993 |
| WO | WO93/13137 A1 * | 7/1993 |
| WO | WO96/02258 A1 * | 2/1996 |
| WO | WO 96/02258 A1 * | 2/1996 |
| WO | WO96/13282 | 5/1996 |
| WO | WO 96/13284 A1 * | 5/1996 |
| WO | WO96/13284 A1 * | 5/1996 |
| WO | WO98/50050 | 11/1998 |
| WO | WO00/71136 A | 11/2000 |
| WO | WO01/98206 A1 | 12/2001 |

OTHER PUBLICATIONS

Tarsi et al., "Inhibition of *Streptococcus mutans* Adsorption to Hydroxyapatite by Low-molecular-weight Chitosans," Journal of Dental Research, 76(2), 665-672 (Feb. 1997).*

D. Venes et al. (eds.), TaberÖs Cyclopedic Medical Dictionary, 19th Edition, F. A. Davis Co., Philadelphia, PA, 2001, only pp. 46, 47, 750 and 1077 supplied.*

Sanzgiri et al., "Targeting Polysaccharide-Methotrexate Conjugates to the Rat Brain," *Polymers for Advanced Technologies*, 3(6), 317-321 (1992 ); Chemical Abstracts, 121(2), p. 582, Abstr. No. 17814h (Jul. 11, 1994).*

D. Venes et al. (eds.), *Taber's Cyclopedic Medical Dictionary, 19th Edition*, F. A. Davis Co., Philadelphia, PA, 2001, only pp. 46, 47, 750 and 1077 supplied.*

Sanzgiri et al., "Targeting Polysaccharide-Methotrexate Conjugates to the Rat Brain," *Polymers for Advanced Technologies*, 3(6), 317-321 (1992†); Chemical Abstracts, 121(2), p. 582, Abstr. No. 17814h (Jul. 11, 1994).*

Brecht, M. et al., "Increased hyaluronate synthesis is required for fibroblast detachment and mitosis," *Biochem, J.* 239:445-450 (1986).

(Continued)

*Primary Examiner*—L. E. Cramer
(74) *Attorney, Agent, or Firm*—Ralph A. Loren, Esq.; Edwards Angell Palmer & Dodge, LLP

(57) ABSTRACT

The present invention relates to a method of inhibiting cellular and protein attachment to substrates by applying a composition containing an effective amount of adherent N,O-carboxymethylchitosan to a substrate with such that cellular and protein attachment are prevented or greatly reduced.

9 Claims, 8 Drawing Sheets

OTHER PUBLICATIONS

Docherty, R. et al., "Glycosaminoglycans facilitate the movement of fibroblasts through three-dimensional collagen matrices," *J. Cell Sci.* 92:213-270 (1989).

Hoekstra, D., yaluronan-modified surfaces for medical devices, *Medical devices & diagnostic Industry*, 48-58 (1989); (Feb. 1999).

Lynn, L.H. et al., "Effects of hyaluronan on collagen fibrillar matrix contraction by fibroblasts," *J. of Biomedical Materials Research*, 28:123-132 (1994).

Aldemann-Grill et al. (1990) "Chemotactic Migration of Normal Dermal Fibroblasts Towards Epidermal Growth Factor and Its Modulation by Platelet-Derived Growth Factor and Transforming Growth Factor-Beta" *Eur. J. Cell Biol.* 51:322-326;(Iss. No. 2, Apr. 1990).

Borah et al. (1995) "Wound Epithelialization is Accelerated by N,O-Carboxymethyl Chitosan" *Amereican Burn Assoc. 27th Annual Mtg.*, Albuquerque, NM; (Apr. 1995).

Buchholz et al. (1984) "Antibiotic-loaded Acrylic Cement: Current Concepts" *Clin. Orthop. & Rel. Res.* 190:96-108; (Nov. 1984).

Buchholz et al. (1981) "Management of Deep Infection of Total Hip Replacement" *J. Bone & Joint Surgery* 63B(3):342-353.

Canalis et al. (1988) "Growth Factors and the Regulation of Bone Remodeling" *J. Clin. Invest.* 81:277-281; (Feb. 1988; Issue No. 2).

Chandrasekaran et al. (1982) "Dissolution-Controlled Transport from Dispersed Matrixes" *J. Pharmaceut. Sci.* 71(12):1399-1402; (Dec. 1982).

Chandy et al. (1991) "Biodegradable Chitosan Matrix for the Controlled Release of Steroids" *Biomat., Art. Cells & Immob. Biotech.* 19(4):745-760.

Christian et al. (1989) "Reconstruction of Large Diaphyseal Defects, without Free Fibular Transfer, in Grade-IIIB Tibial Fractures" *J. Bone & Joint Surg.* 71-A(7):994-1004; (Aug. 1989).

Dash et al. (1992) "An Implantable Dosage Form for the Treatment of Bone Infections" *Pharmaceutical Research* 9(8):993-1002; (Aug. 1992).

Davies et al. (1988) "N, O-Carboxymethl Chitosan, A New Water Soluble Chitin Derivative" *Proceed. Int'l Chitin-Chitosan Conference*; Aug. 22-24, 1988; Trondheim, Norway.

Golub et al. (1994) "Treating Peridontal Diseases by Blocking Tissue-Destructive Enzymes" *JADA* 125:163-171; (Feb. 1994).

Goodson et al. (1983) "Monolithic Tetracycline-containing Fibers for Controlled Delivery to Periodontal Pockets" *J. Periodontol.* 54(10):575-579; (Oct. 1983).

Greco et al. (1991) "Fibrin-antibiotic mixtures: An in vitro study assessing the possibility of using a biological carrier for local drug delivery" *J. Biomed. Mat. Res.* 25(1):39-51;(Jan. 1991).

Greenhalgh et al. (1990) "PDGF and FGF Stimulate Wound Healing in Genetically Diabetic Mouse" *Amer. J. Pathol.* 136(6):1235-1246; (Jun. 1990).

Hattori (1990) "Bone Morphogenetic Protein-BMP: Experimental Investigations of Osteogenesis and Chondrogenesis by Implant of BMP-Fibrin Glue Mixture" *J. Jpn. Orthop. Assoc.* 64:824-834;(Sep. 1990).

Hauschka et al. (1986) "Growth Factors in Bone Matrix" *J. Biol. Chem.* 261(27):12665-12674; (Sep. 25, 1986).

Hayek et al. (1987) "An In Vivo Model For Study of the Angiogenic Effects of Basic Fibroblast Growth Factor" *Biochem. & Biophys. Res. Comm.* 147(2):876-880; (Sep. 15, 1987).

Higuchi (1963) "Mechanism of Sustained-Action Medication-Theoretical Analysis of Rate of Release of Solid Drugs Dispersed in Solid Matrices" *J. Pharmaceut. Sci.* 52(12):1145-1149; (Dec. 1963).

Kawamura et al. (1988) "Human Fibrin is a Physiologic Delivery System for Bone Morphogenetic Protein" *Clin. Orthop. & Rel. Res.* 235:302-310: (Oct. 1988).

Klokkevold et al. (1992) "Effect of Chitosan on Lingual Hemostasis in Rabbits with Platelet Dysfunction Induced by Epoprostenol" *J. Oral Maxillofac. Surg.* 50:41-45;(Jan. 1992).

Knighton et al. (1986) "Classification and Treatment of Chronic Nonhealing Wounds" *Ann. Surg.* 204(3):322-330; (Sep. 1986).

Kram et al. (1991) "Antibacterial Effects of Fibrin Glue-Antibiotic Mixtures" *J. Surg. Res*: 50:175-178;(Feb. 1991).

Kristl et al. (1993) "Hydrocolloids and Gels of Chitosan as Drug Carriers" *Int'l J. Pharmaceut.* 99:13-19.

Ksander et al. (1990) "The Effect of Platelet Releasate on Wound Healing in Animal Models" *Amer. Acad. Dermatol.* 22(5):781-791; (Part 1, May 1990).

Luyten et al. (1989) "Purification and Partial Amino Acid Sequence of Osteogenin, a Protein Initiating Bone Differentiation" *J. Biol. Chem.* 264(23):13377-13380; (Aug. 15, 1989).

Lynch et al. (1989) "Growth Factors in Wound Healing" *J. Clin. Invest.* 84:640-646; (Aug. 1989).

Mackey et al. (1982) "Antibiotic Loaded Plaster of Paris Pellets" *Clin. Orthop. & Rel. Res.* 167:263-268; (Jul. 1982).

Majid et al. (1985) "Gentamicin-PMMA Beads in the Treatment of Chronic Osteomyelitis" *Acta. Orthop. Scand.* 56:265-268; (Jun. 1985).

McDermott et al. (1986) "Experimental Use of a New Gentamycin Impregnated Gel" *Canadian Medical Assoc. Conference Abstract*; (Jun. 1-5, 1986; Edmonton, Alberta).

Menaché et al. (1991) "Coagulation Factor IX (human)" in *Hemophilia and Von Willebrand's Disease in the 1990's: A New Decade of Hopes and Challenges*, Lusher et al., eds. (Elsevier Science Publishers B.V., Amsterdam) pp. 301-305; (Aug. 14-19, 1990; Washington, DC).

Menon et al. (1995) "Development of a Composite of Hydroxylapatite and Chitosan as a Bone Graft Substitute" *Proceedings of the 14th southern biomedical Engineering Conference*, Shreveport, LA; (Apr. 7-9, 1995).

Miclau et al. (1993) "In Vitro Pharmakinetics of Antibiotic Release from Locally Implantable Materials" *J. Orthop. Res.* 11:627-632; (Issue No. 5).

Redl et al. (1983) "In Vitro Properties of Mixtures of Fibrin Seal and Antibiotics" *Biomaterials* 4:29-32; (Issue No. 1, Jan. 1983).

Sakurai et al. (1992) "Controlled Release of Sisomicin from Fibrin Glue" *J. Controlled Release* 18:39-43; (Jan. 1992; Issue No. 1).

Schlag et al. (1988) "Fibrin Sealant in Orthopedic Surgery" *Clin. Orthop. & Rel. Res.* 227:269-285; (Feb. 1988).

Schrenk et al. (1987) "Fibrin Glue Coating of e-PTFE Prostheses Enhances Seeding of Human Endothelial Cells" *Thorac. Cardiovasc. Surgeon* 35:6-10; (Issue No. 1; Feb. 1987).

Schultz et al. (1987) "Epitheial Wound Healing Enhanced by Transforming Growth Factor-α and Vaccinia Growth Factor" *Science* 235:350-352; (Jan. 16, 1987).

Schwartz et al. (1989) "The Influence of Fibrin Sealant on Demineralized Bone Matrix-Dependent Osteoinduction" *Clin. Orthop. & Rel. Res.* 238:282-287; (Jan. 1989).

Thacharodi et al. (1993) "Release of Nifediphine through Crosslinked Chitosan Membranes" *Int'l J. Pharmaceut.* 96:33-39; (Issues 1-3; Jul. 31, 1993).

Thompson et al. (1989) "Heparin-binding Growth Factor 1 Induces the Formation of Organoid Neovascular Structures In Vivo" *Proc. Natl. Acad. Sci.* 86:7928-7932;(Oct. 1989).

Thompson et al. (1988) "Site-Directed Neovessel Formation in Vivo" *Science* 241:1349-1352; (Sep. 9, 1988).

Tsuboi et al. (1990) "Recombinant Basic Fibroblast Growth Factor Stimulates Wound Healing in Healing-impaired db/db Mice" *J. Exp. Med.* 172:245-251;(Jul. 1, 1990).

Urist et al. (1973) "Bone Morphogenesis in Implants of Insoluble Bone Gelatin" *Proc. Natl. Acad. Sci.* 70(12)3511-3515; (Dec. 1973).

Van Brunt et al. (1988) "Growth Factors Speed Wound Healing" *Bio/Tech.* 6:25-29; (Issue No. 1; Jan. 1988).

Wang et al. (1991) "Bone Morphogenetic Proteins and Bone Repair" *J. Cell. Biochem.* Supp 15F:161; (Abstract # Q020; Apr. 1-7, 1991).

Zilla et al. (1989) "Use of Fibrin Glue as a Substrate for in Vitro Endothelialization of PTFE Vascular Grafts" *Surgery* 105(4):515-522. (Apr. 1989).

van der Lubben, et al. (2001) "Chitosan and its Derivatives in Mucosal Drug and Vaccine Delivery" *European Journal of Pharmaceutical Sciences* 14: 201-207.

Kumar (2000) "A Review of Chitin and Chitosan Applications" *Reactive & Functional Polymers* 46: 1-27.

The Supplementary Partial European Search Report (EP02721645).

The Supplementary Partial European Search Report (EP00936059).

\* cited by examiner

ADHESIVE N,O-CARBOXYMETHYLCHITOSAN COATINGS WHICH INHIBIT ATTACHMENT OF SUBSTRATE-DEPENDENT CELLS AND PROTEINS

REFERENCE TO RELATED APPLICATIONS

This application is a Divisional which claims the priority of U.S. patent application Ser. No. 10/672,072, filed Sep. 25, 2003 now U.S. Pat. No. 6,894,035, which is a Continuation in Part of U.S. patent application Ser. No. 09/315,480, filed May 20, 1999, now U.S. Pat. No. 6,645,947B1, the entirety of which is incorporated herein by reference.

BACKGROUND OF THE INVENTION

The attachment of cells and proteins to substrates is a well-known problem that has presented itself in a number of contexts. For example, in cell cultures to produce antibodies, fibroblasts attach to extracellular matrix proteins bound to the tissue culture substrate. Similarly, in urinary catheters, bacterial cells attach to the walls of the catheter; in arterial catheters, platelets attach to the tip of the catheter; and in contact lenses, proteins coat the surfaces of the lenses.

Various bioadhesives are known in the art. U.S. Pat. No. 4,615,697, issued to Robinson et al., defines a bioadhesive as a material that requires a force of at least about 50 dynes/cm$^2$ to separate two adhered, freshly excised pieces of rabbit stomach, following the procedure disclosed therein. The bioadhesive disclosed in Robinson et al. is a water-swellable, but water insoluble, fibrous, cross-linked carboxy-functional polymer.

Various attempts to ameliorate the problem of attachment of cells and proteins to substrates have been employed, but none have been found to be satisfactory. It would be desirable to solve this problem using a biocompatible substance that is adherent to substrates and inhibits cellular and protein attachment.

Certain cells, such as macrophages and fibroblasts, are referred to as "substrate-dependent cells" because they are active and proliferate only when attached to a surface or substrate. The attachment occurs via a family of proteins ("attachment molecules or proteins"), such as vitronectin and fibrinectin, which are found in the extracellular matrix. A surface that is coated with a material that is strongly adhesive may inhibit the attachment of substrate dependent cells by blocking attachment of extracellular matrix proteins. Hence, adhesive materials, as described herein, are useful in compositions or can form devices that inhibit the attachment of certain proteins and certain types of cells.

SUMMARY OF THE INVENTION

The present invention features a method of inhibiting cellular attachment to substrates. The invention is based, in part, on the discovery of adherent coatings of N,O-carboxymethylchitosan ("NOCC"), and in particular that adherent coatings of NOCC may be applied to various substrates, such as mammalian tissue, so as to inhibit attachment of other cells, such as substrate dependent cells. Further, it has been discovered that these adherent coatings of NOCC may be used in other areas where inhibition of cell or protein attachment is desirable, such as in the preparation of cell populations, on medical devices, and with cell-based products. The invention also has application to the inhibition of the attachment of proteins to surfaces.

The present invention provides a composition that is adherent to a variety of synthetic materials and mammalian tissues. The present invention also provides a method of inhibiting cellular and protein attachment to a substrate by applying adherent coatings of NOCC to the substrate such that the attachment of cells and proteins is inhibited. The amount of adherent NOCC in the composition should be effective to inhibit the attachment of substrate-dependent cells, preferably in a concentration of 0.05–5%(w/v), most preferably in a concentration of 0.1–2.5%(w/v).

In one embodiment, the invention provides a composition and method of inhibiting attachment of substrate-dependent cells to a substrate by applying a composition containing adherent NOCC to a substrate such that attachment of substrate-dependent cells is inhibited. The method may be applied to inhibit substrate-dependent cell attachment to mammalian tissue, medical devices, fermentation units, bioreactors and solid supports. In preferred embodiments, the substrate-dependent cells which are inhibited include fibroblasts, macrophages, epithelial cells, and endothelial cells.

In another embodiment, the invention provides a composition and method of inhibiting attachment of proteins to a substrate by applying a composition containing adherent NOCC to a substrate such that attachment of proteinaceous material is inhibited. The method may be applied to inhibit protein attachment to contact lenses, medical devices, fermentation units, bioreactors and solid supports.

In another embodiment, the invention may be used in a method of obtaining a population of cells, e.g., mammalian cells, by supplementing culture media with adherent NOCC, growing the population of cells in the supplemented media, and allowing the cells to grow or differentiate, such that substrate-dependent cells do not proliferate within the cell population.

In another embodiment, the invention provides a method of obtaining cells suitable for use in protein or antibody production by supplementing culture media with adherent NOCC and growing the cells in the supplemented media, such that intercellular attachment (or clumping) within the cell population is inhibited and production of proteins or antibodies is enhanced.

In yet another embodiment, the invention provides a method of inhibiting attachment of inflammatory cells and platelets to a medical device by coating said device with a composition containing adherent NOCC, such that platelet or inflammatory cell attachment to the medical device is inhibited. In preferred embodiments, the internal medical device is either a stent or shunt. In other preferred embodiments, the inflammatory cell includes fibroblasts, macrophages, and monocytes.

In still another embodiment, the invention includes a method of inhibiting fibroblast attachment in a cell-based product in contact with a solid support by introducing adherent NOCC into the cell based product such that fibroblast attachment is inhibited.

In another embodiment, the invention provides a composition and method of delivering drugs, proteins, and other therapeutic agents from an adhesive device or composition that is adherent to soft (mucosal or non-mucosal) tissue or hard tissue. In preferred embodiments, the adherent delivery device can be used as a buccal, oral, vaginal, inhalant, or the like delivery system. The device can be in a variety of forms including solutions, creams, pellets, particles, beads, gels, and pastes.

DETAILED DESCRIPTION OF THE INVENTION

Figure 1:
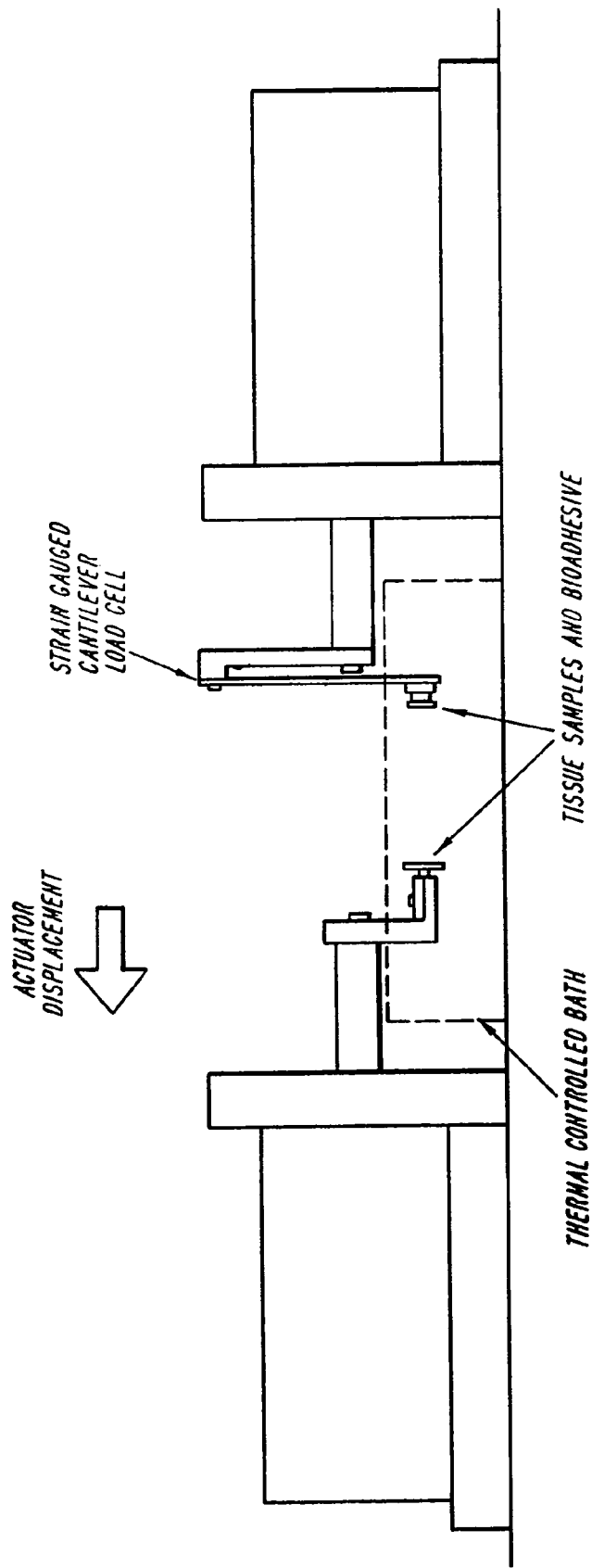
FIG. 1 is a schematic of the apparatus used in Example 1.

The present invention relates to the inhibition of cellular and protein attachment to various substrates. The method of the invention uses an adherent coating of N,O-carboxymethylchitosan ("NOCC") which provides unexpected benefits in inhibiting cellular and protein attachment.

NOCC is a derivative of chitin, which is found in the shells of crustaceans and many insects. Chitin and its derivatives are normally biocompatible, naturally resorbed by the body, and have previously been used for sustained drug release, bone induction and hemostasis (Chandy and Sharma, *Biomat. Art. Cells & Immob. Biotech.* 19:745–760 (1991); Klokkevold, P. et al., *J. Oral Maxillofac. Sur.* 50:41–45 (1992)). Due to its prevalence, chitin may be obtained relatively cheaply, largely from waste products. As disclosed in U.S. Pat. No. 4,619,995, issued to Hayes, the entire contents of which are hereby incorporated by reference, NOCC has carboxymethyl substituents on some of both the amino and primary hydroxyl sites of the glucosamine units of the chitosan structure. NOCC may be used in an uncrosslinked form as a solution or may be cross-linked or complexed into a stable gel. Because of its advantageous physical properties, and its relative low cost, NOCC presents advantageous properties for use in inhibiting cellular and protein attachment.

Definitions

The term "inhibit," or any form thereof, is defined in its broadest sense and includes minimize, prevent, repress, suppress, curb, constrain, restrict and the like.

The terms "adherent NOCC" or "an adherent coating of NOCC" mean a coating or composition of NOCC that exhibits an adhesion between freshly excised tissue of at least about 100 dynes/cm$^2$, using the procedure described in Example 1.

The term "substrate" refers to any object to which cells can attach. Examples of substrates include, without limitation, mammalian tissue (including both hard tissue, such as bone, and soft tissue, such as mucosal and non-mucosal tissue), non-mammalian tissue, mammalian and non-mammalian cells (including both eukaryotic and prokaryotic organisms), medical devices, fermentation units, bioreactors, and solid supports, such as cell culture plates.

The term "substrate-dependent cells" means cells that are only active when attached to a substrate. Examples of substrate dependent cells include, without limitation, fibroblasts, macrophages, epithelial cells, somatic cells, and endothelial cells.

The term "medical device" means any device which is implanted in the body for medical reasons or which has a portion of the device extending into the body (like a catheter) as well as devices which provide a medical benefit when attached to, or are in contact with, the body. Examples of medical devices include, without limitation, catheters, contact lenses, stents, shunts, breast implants and pacemakers.

The term "inflammatory cell" means a cell involved in the non-specific immune response to any type of body injury. Examples of inflammatory cells include, without limitation, fibroblasts, macrophages, eosinophils, neutrophils, monocytes and lymphocytes.

The term "cell-based product" means any product that contains cell. Examples of cell-based products include, without limitation, blood, plasma, aliquots of cell cultures, and the like.

The invention provides a method of inhibiting attachment of substrate-dependent cells or proteins to a substrate by applying a composition containing adherent NOCC to a substrate such that attachment of the substrate-dependent cells or protein is inhibited. In preferred embodiments, the method is applied to inhibit substrate-dependent cell attachment to mammalian tissue, medical devices, fermentation units, bioreactors and solid supports. In preferred embodiments, the substrate-dependent cells which are inhibited include fibroblasts, macrophages, epithelial cells, and endothelial cells.

The invention also may be used in a method of obtaining a population of cells, e.g., mammalian cells, by supplementing culture media with adherent NOCC, growing the population of cells in the supplemented media, and allowing the cells to grow or differentiate, such that substrate-dependent cells do not proliferate within the cell population.

The invention further provides a method of increasing the efficiency of protein or antibody production by supplementing culture media with adherent NOCC and growing the cells in the supplemented media, such that intercellular attachment within the cell population is inhibited and production of protein or antibodies is enhanced.

The invention also provides a method of inhibiting attachment of inflammatory cells or proteins to a medical device by coating said device with a composition containing adherent NOCC, such that inflammatory cell or protein attachment to the medical device is inhibited. In preferred embodiments, the medical device is a catheter, a contact lens, a stent, pacemaker, breast implant, or a shunt. The method is useful for preventing attachment of a variety of inflammatory cells including fibroblasts, macrophages, monocytes, as well as proteins such as albumin.

In still another embodiment, the invention includes a method of inhibiting fibroblast attachment in a cell-based product in contact with a solid support by introducing the cell based product to an adherent coated solid support such that fibroblast attachment is inhibited.

The adherent NOCC used in the present invention may take many forms. For example, adherent NOCC may be used in a solution, a hydrogel, a paste, a rehydratable film, cream, foam, or a sponge. These forms are prepared by methods well known to those of ordinary skill in the art.

The adherent NOCC used in the present invention may be the parent compound or may be cross-linked. Cross-linked adherent NOCC may be either covalently cross-linked or ionically cross-linked. Various methods of cross-linking NOCC are known in the art and are within the scope of this invention. In addition, the degree to which the adherent NOCC is cross-linked may be optimized for specific applications by one of ordinary skill without undue experimentation. It has been found that the degree of cross-linking is roughly inversely proportional to the adhesiveness of the coating. That is, the greater the degree of cross-linking of the adherent NOCC, the lesser degree of adherence. In preferred embodiments, the degree of cross-linking is less than 1:5 (moles cross-linking agent to moles, NOCC monomer), more preferably between 1:100 and 1:1000 on a molar basis.

Figure 2:
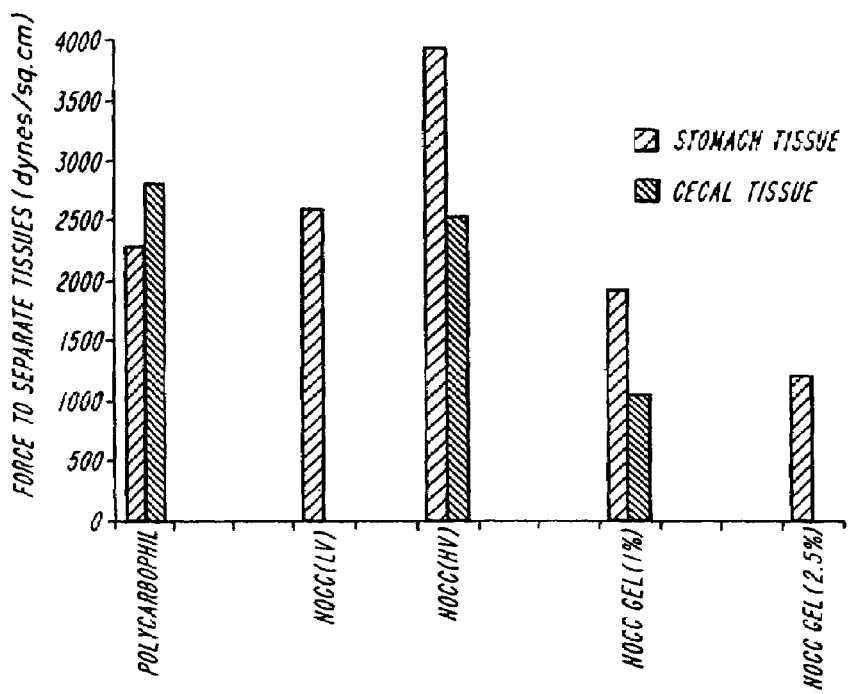
FIG. 2 is a bar graph showing the results of Example 1.

The bioadhesive strength of several adherent NOCCs was compared to that of polycarbophil, a cross-linked acrylic acid polymer available from B.F.Goodrich. As more fully described in Example 1, solutions of low and high viscosity NOCC were prepared, as well as hydrogels of high viscosity NOCC. The bioadhesive was applied to stomach and cecal tissue samples and the bioadhesive strength was measured according to a modified version of the procedure disclosed in U.S. Pat. No. 4,615,697, which is hereby incorporated by reference. The transfer of polymer to both tissue surfaces indicated that the adhesive force of the polymer exceeded the cohesive force. A summary of results appears in Tables 1 and 2, and FIG. 2. In preferred embodiments, the bioadhesive strength of adhesive NOCC coatings of the invention is desirably greater than at least about 1000 dynes/cm$^2$, more preferably greater than at least about 2000 dynes/cm$^2$, and most preferably greater than at least about 3000 dynes/cm$^2$.

Both the low viscosity and high viscosity NOCC polymer solutions in citrate buffer behaved similarly to polycarbophil when applied as a coating to the mucosal surface of stomach tissue (Table 1). This was also true for similar solutions of NOCC using phosphate buffered saline instead of citrate buffer as well as non-mucosal, cecal tissue (Table 2). It was observed that as NOCC was cross-linked the cohesion of the materials increased and the adhesion decreased. The loss of adhesion was dependent on the extent of cross-linking. These findings are likely attributable to the fact that cross-linking adherent NOCC introduced more structure into the polymer, which consequently restricted interactions with the tissue surface. The cross-linking also joined the polymer chains together, resulting in increased cohesiveness.

Figure 5:
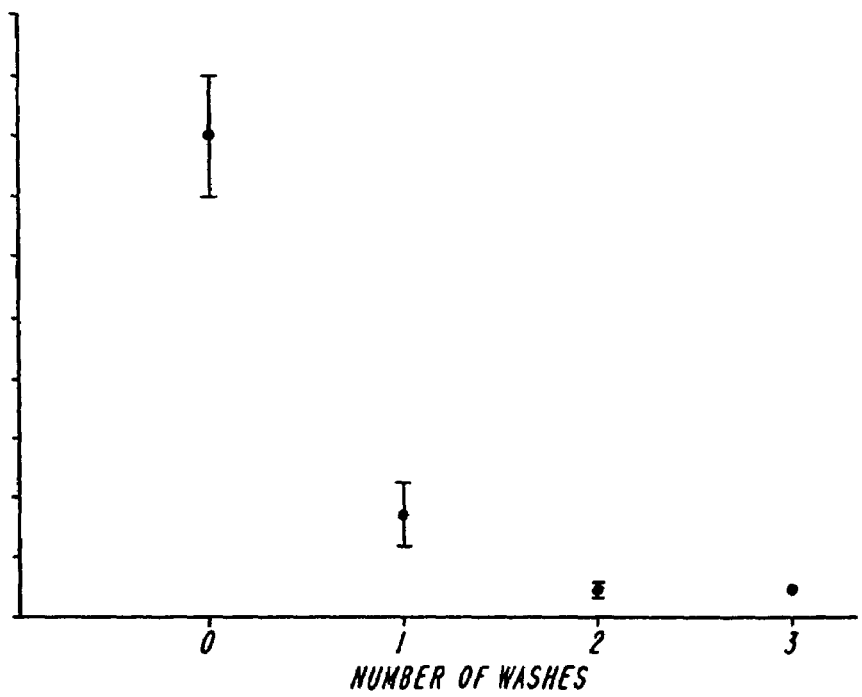
FIG. 5 is graph showing the total volume of $^{125}$I-NOCC adhered to rat femur, as calculated using Equation 3.

The ability of NOCC to adhere to bone tissue was also studied. The results indicate that NOCC adheres to bone tissue (FIG. 5). After the third wash, $9.5 \times 10^{-3} \pm 0.002$ µL/mm$^2$ (or about 0.1 µg NOCC/mm$^2$) of $^{125}$I labeled NOCC remained adhered to the rat femur.

Surprisingly, the adhesive NOCC coatings of the present invention have been shown to inhibit cellular attachment of substrate dependent cells. The adherent NOCC coatings of the present invention thus have applicability in a multitude of areas. In addition, adherent NOCC coatings may be applied to either hard or soft mammalian tissue, such as bone or stomach tissue. Alternatively, adherent NOCC coatings may be applied to non-biological substrates, such as medical devices and solid supports. Examples of such substrates include stents, shunts, contact lenses, microtiter plates, and cell culture plates.

Typically, fibroblasts in a cell or tissue culture adhere to extracellular matrix (ECM) proteins that are bound to the culture substrate (usually plastic). The ECM proteins in culture typically come from the culture medium, which is supplemented with serum to provide these proteins as well as other factors necessary for cell growth. Alternatively, if there are no ECM proteins in the culture medium, fibroblasts will secrete their own ECM proteins and adhere to them. A normal, adhered fibroblast has a very characteristic morphology: it flattens and exhibits cellular appendages or processes extending from the cell over the substrate surface, which indicates fibroblast adherence to the substrate (FIG. 6a).

Figure 6:
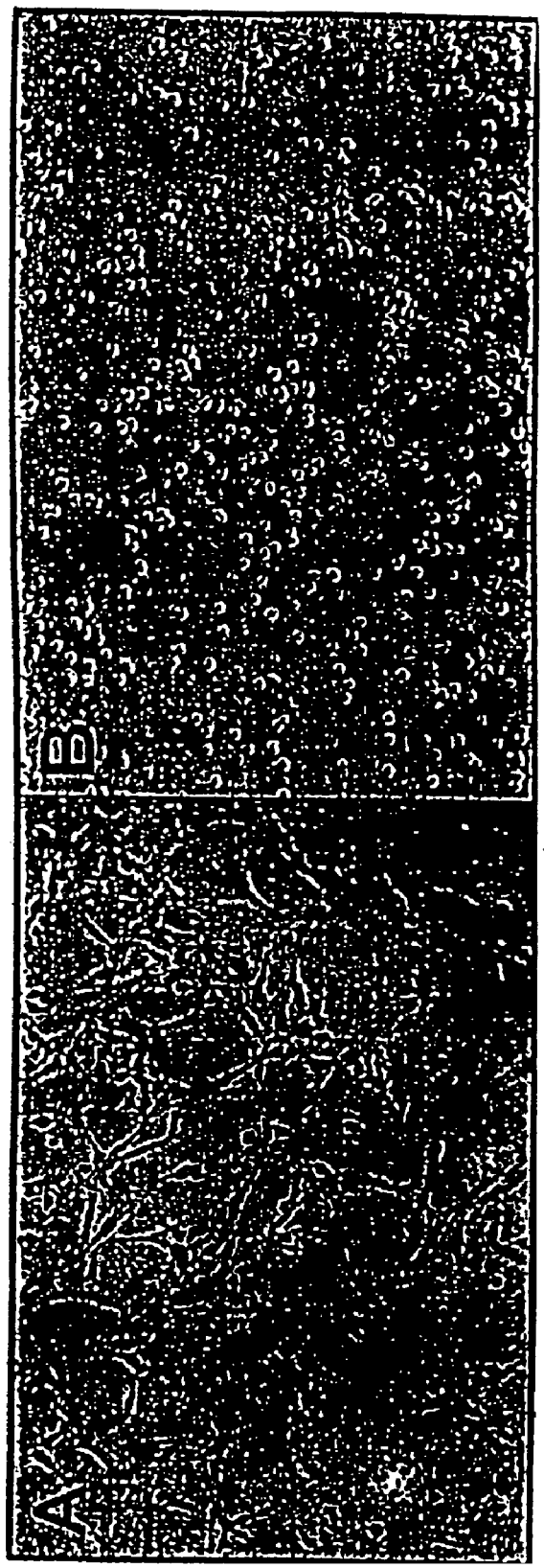
FIG. 6 shows the morphological difference between fibroblasts grown in the absence of NOCC (6a) and fibroblasts grown in the presence of NOCC (6b).

The present invention takes advantage of the observation that substrate-dependent cells, e.g., fibroblasts, plated in tissue culture media in the presence of adherent NOCC coating do not have the characteristic morphology and do not exhibit processes indicating attachment of the cell (FIG. 6b).

Figure 7:
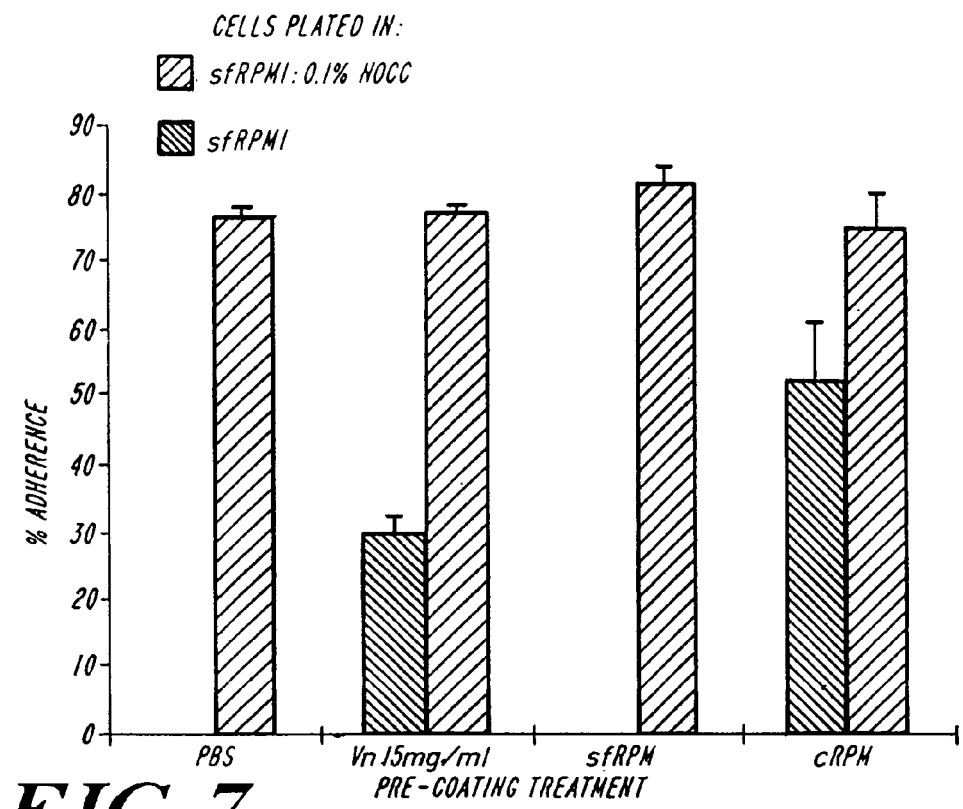
FIG. 7 is a bar graph showing a comparison of adherence by fibroblasts grown in the presence and absence of NOCC, under various pre-coating conditions.

Initial observations of fibroblast morphology in the presence or absence of adherent NOCC in the medium, revealed that when fibroblasts were plated in serum-free media without adherent NOCC they consistently displayed an "adherent" morphology, viz. the cells were flattened with complex processes. As described more fully in Example 3, fibroblasts were plated on tissue culture plates, either in the presence or absence of adherent NOCC, under four different coating conditions. Irrespective of the coating treatment, approximately 80% of cells observed looked like normal cultured fibroblasts in the absence of adherent NOCC. In contrast, when fibroblasts were plated in the presence of adherent NOCC, the number of cells displaying the adherent morphology was significantly reduced. In fact, in the instance where no ECM proteins were present, no cells adhered in the presence of adherent NOCC. Where ECM proteins were present, some cell adherence was observed, but the adherence was significantly less than that which occurred in the absence of adherent NOCC (FIG. 7).

Figure 8:
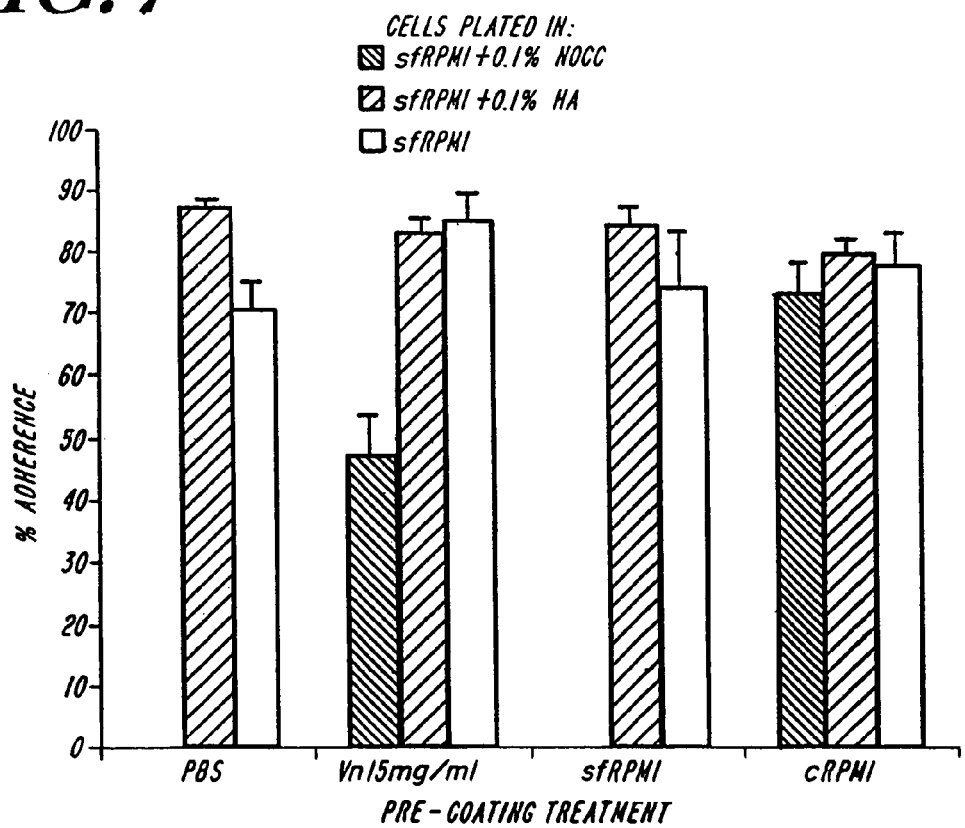
FIG. 8 is a bar graph showing a comparison of adherence by fibroblasts grown in the presence and absence of NOCC, under various pre-coating conditions.

Hyaluronic acid (HA) was also tested in this system, to determine whether it had similar effects to NOCC. When a similar morphological examination was performed on cells plated in sfRPMI (serum free or protein free RPMI medium) containing 0.1% HA, it was observed that the HA did not have the same effect on fibroblast morphology (FIG. 8).

Figure 9:
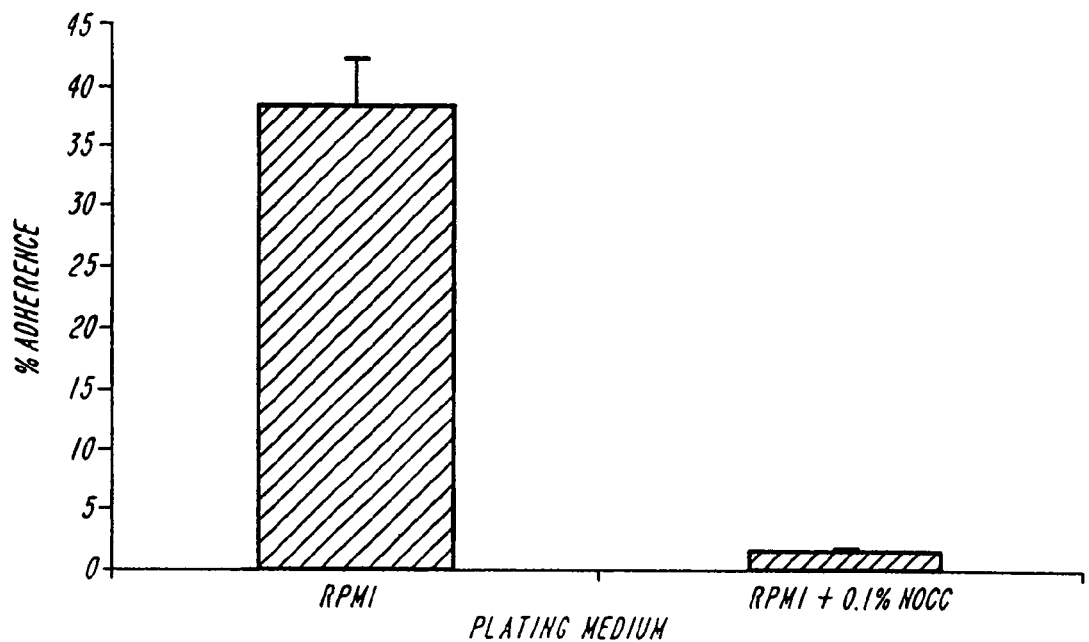
FIG. 9 is a bar graph showing a comparison of adherence by fibroblasts grown in the presence and absence of NOCC, as determined by $^{51}$Cr release assay.

Fibroblast adherence was also measured quantitatively, using a $^{51}$Cr adhesion assay (the $^{51}$Cr release assay). The results confirmed that adherent NOCC blocks adhesion of 3T3 fibroblasts to plastic, by more than 90% using this assay (FIG. 9). This result, taken together with the previous work, suggests that adherent NOCC adheres to the substrate and interferes with the deposition of ECM proteins in a competitive manner.

Figure 10:
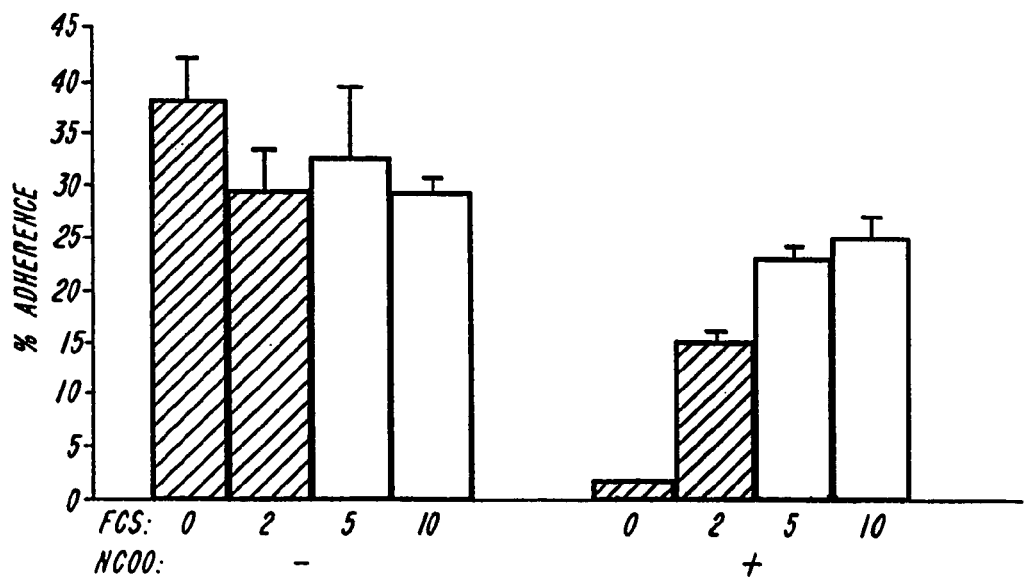
FIG. 10 is a bar graph showing a comparison of adherence by fibroblasts grown in the presence and absence of NOCC, as determined by $^{51}$Cr release assay.

A competitive assay was performed using media supplemented with varying concentrations of fetal calf serum (FCS), which contains the ECM proteins of interest, and in the presence or absence of NOCC. As expected, it was found that the presence of FCS in the plating medium reversed the inhibitory effect of adherent NOCC on fibroblast adhesion in a dose dependent manner, where 10% FCS fully restored binding of 3T3 to the plates in the presence of NOCC (FIG. 10). There are two possible explanations for this effect: 1) adherent NOCC prevents fibroblast adhesion to the ECM proteins which bind to the plate, or 2) adherent NOCC prevents the binding of ECM proteins to the plate in a competitive manner.

Figure 11:
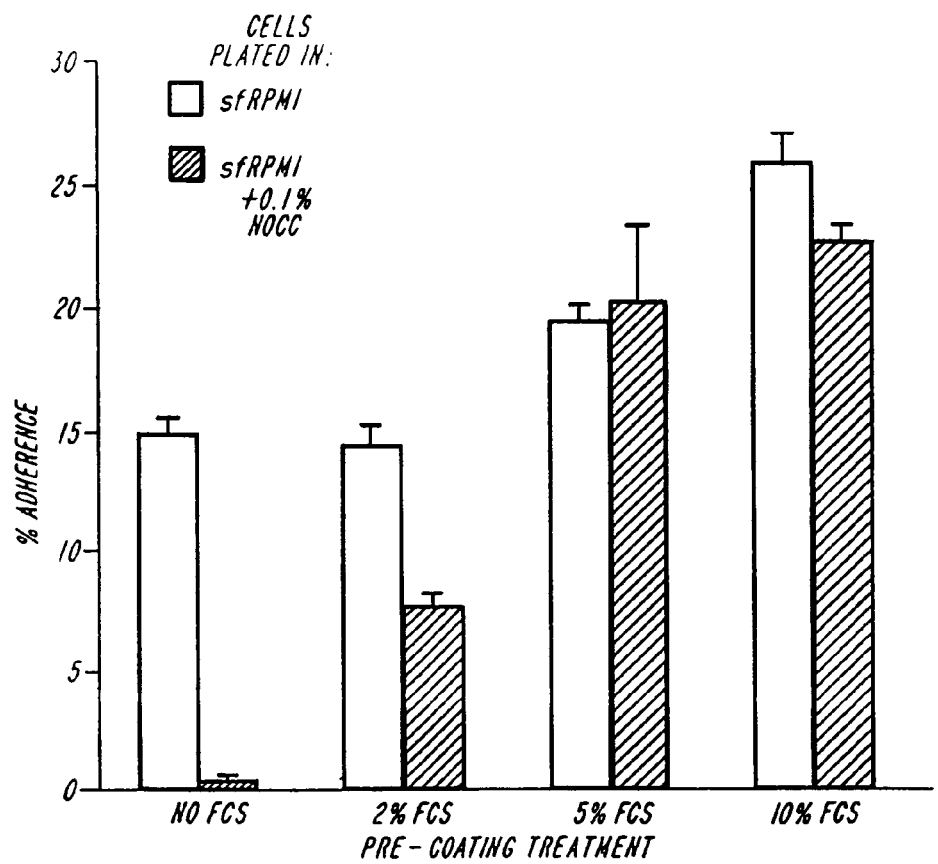
FIG. 11 is a bar graph showing a comparison of adherence by fibroblasts grown in the presence and absence of NOCC under various pre-coating conditions, as determined by $^{51}$Cr release assay.
Figure 12:
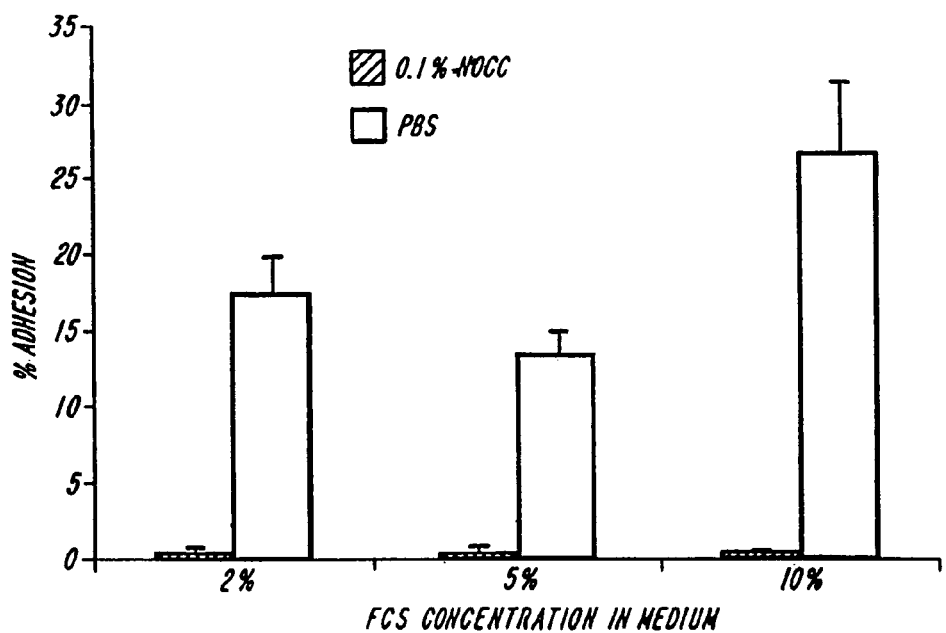
FIG. 12 is a bar graph showing a comparison of adherence by fibroblasts grown in plates that were pre-coated with and without NOCC, as determined by using cells labeled with tritiated thymidine.

To address these possibilities, tissue culture plates were pre-coated with serum-free medium containing varying concentrations of FCS. The presence of adherent NOCC did not interfere with the adhesion of fibroblasts to the FCS coated plates, which confirmed that adherent NOCC does not inhibit adhesion of fibroblasts to ECM proteins already deposited on the plate (FIG. 11). This result was confirmed by coating tissue culture plates with an adherent NOCC coating. The results (FIG. 12) demonstrate that fibroblast adherence to adherent NOCC coated plastic is eliminated in the presence of FCS. This result supports the hypothesis that adherent NOCC binds to the plastic plate surface and prevents the deposition or attachment of ECM proteins. Thus, adherent NOCC may inhibit cellular attachment by preventing the deposition of ECM proteins rather than by inhibiting the adhesion of fibroblasts to the ECM proteins. In the absence of the ECM protein network, fibroblasts are unable to bind to a substrate.

The following, non-limiting examples will further elucidate the invention.

EXAMPLE 1

In this example, the bioadhesive strength of several adherent NOCC coating compositions is compared to that of polycarbophil. Polycarbophil (B.F. Goodrich, Akron, Ohio) was prepared as a 4% w/v solution in both 0.2M citrate buffer (pH 4.8) and 0.9% saline (pH 6.8). Low viscosity ("LV") NOCC (240 cps, Brookfield spindle 3, 50–100 rpm) was prepared as 4% w/v solution in citrate buffer (pH 5.6). High viscosity ("HV") NOCC (P78NOCC1) was prepared as 2.5% w/v solution in citrate buffer (pH 5.6). High viscosity NOCC was prepared as 1% and 2.5 % in citrate buffer (pH 5.6–5.7), autoclaved and cross-linked (1:500). HV NOCC was also prepared as 2.5% solution in phosphate buffered saline (PBS). Gels were formed from 1% HV NOCC by cross-linking (1:100) in PBS and by cross-linking (1:250) in saline following autoclaving.

Both stomach and cecal tissues from Sprague-Dawley rats were harvested immediately prior to testing and were kept moist in saline solution. Tissue samples were mounted on circular plastic disks with the inner surfaces of stomach tissues and the outer surfaces of cecal tissues exposed. Tissue samples were held in place with a suture around the end of the plastic disks. The plastic disks were obtained from the plungers of 3 and 5 ml syringes; the diameters of the disks were 7.0 (surface area of 38.5 mm$^2$) and 9.5 mm (surface area of 70.9 mm$^2$), respectively. The tissue holders were attached to a cantilever load cell and to the actuator of an MTS servohydraulic material testing machine (see FIG. 1).

The temperature compensated load cell was wired into a Daytronic 3720 Strain Gauge Conditioning Unit in a half bridge configuration. Data collection was performed using a Macintosh Centris 650 computer equipped with labVIEW software and a 12 bit NB-MIO-16 data acquisition board. The cantilever load cell was calibrated over the working range of 0–3 grams using a series of proving masses (0.1, 0.23, 0.5, 1 to 3.0 g) verified on a Mettler PJ 360 balance. A least squares calibration curve was determined to convert the resulting output from volts to grams force.

The smaller diameter tissue of the pair of fresh tissue samples received 30 µl of test material. The software was designed to take a zero reading after attaching the tissue samples and applying a coating of the bioadhesive. The testing system actuator was then manually advanced using the displacement potentiometers to bring mating faces into compression while visually monitoring the resulting load level on the computer monitor. The mating faces were allowed to remain compressed at a nominal load of 0.9 g for one minute. The computer then displaced the actuator at a constant rate of 12.0 mm/min, monitoring the distraction force with time. After failure the computer determined the peak distraction load and saved the loading curves to a spreadsheet file.

For repeated testing of the same samples, the tissues were scraped with the side of a syringe needle, rinsed with citrate buffer or water as appropriate and a new aliquot of the same polymer was applied. Fresh tissues were used for each different polymer sample; all samples in citrate buffer were tested on stomach tissue and all samples at neutral pH were tested on cecal tissue. All testing was performed in air.

All polymer samples were applied to the smaller surface area tissue sample at a rate of approximately 1 µl per sq.mm. Following distraction of the actuator, the transfer of polymer to both tissue surfaces indicated that the adhesive force of the polymer exceeded the cohesive force. For example, polycarbophil was adhesive to both cecal and stomach tissue and required a tensile force of 2300–2800 dynes/cm$^2$ to cause failure. The failure was cohesive rather than adhesive since polymer was observed on both tissue surfaces after separation. A summary of results appears in Tables 1 and 2 and FIG. 2.

Both the low viscosity and high viscosity adherent NOCC polymer solutions in citrate buffer behaved similarly to polycarbophil when applied as a coating to the mucosal surface of stomach tissue. Both adherent NOCC samples failed cohesively and required larger forces to achieve tissue separation than for polycarbophil. However, when high viscosity NOCC solutions were cross-linked to form hydrogels, they became more cohesive and failed by detaching from the larger diameter disk at forces of 85% (1% gel) and 53% (2.5% gel) of that of polycarbophil.

The strengths of adhesion to the external surface of the cecum (Table 2) again demonstrated that a solution of NOCC (2.5%-high viscosity) was comparable to polycarbophil. It was also observed that as adherent NOCC was cross-linked the cohesion of the materials increased and the adhesion decreased. The loss of adhesion was dependent on the extent of cross-linking.

It should be noted that polycarbophil measured under the present conditions exhibited twice the adhesive force as reported in U.S. Pat. No. 4,615,697. This is presumably due to testing in air rather than in solution. For both stomach and cecal tissues, adherent NOCC solutions were either comparable to or exceeded the performance of polycarbophil: the force required to achieve failure was equal to or larger than that of polycarbophil and failure was due to cohesion not adhesion.

NOCC hydrogels on both types of tissue were adhesive; however, they were significantly less adhesive than materials that were not cross-linked. They demonstrated an adhesive failure rather than cohesive; also it was observed that increasing the extent of cross-linking decreased the adhesive force. These findings were not surprising since cross-linking adherent NOCC introduced more structure into the polymer which restricted interactions with the tissue surface and also joined the polymer chains together resulting in increased cohesiveness.

Another finding was that both the 2.5% high viscosity NOCC solution and the 1% NOCC gel in citrate were more adhesive than its counterparts in PBS. Without limitation to the present invention, this difference may possibly be explained by the influence of the citric acid environment. At neutral pH, NOCC exists as an anionic species resulting from the presence of negatively-charged carboxylate groups (—COO); the free amines on NOCC are primarily uncharged. By contrast, in acidic citrate buffer (pH 5.6) the amine groups are protonated to form positively-charged ammonium sites (—$NH_3+$) which ionically bind citrate ions. Such salts are described in U.S. Pat. No. 5,412,084, the disclosure of which is incorporated herein by reference. Since citrate has 3 carboxylate groups, 2 of which are negatively-charged at pH 5.6, the net result is that NOCC in acidic citrate has an increased number of carboxylate groups associated with the polymer and, hence, displays an increased bioadhesiveness.

TABLE 1

Bioadhesion of NOCC Formulations to Stomach Tissue.

| Polymer Sample | Tensile Failure Force (grams) | Force to Separate Tissue (dynes/sq · mm) | Adhesive or Cohesive Failure |
|---|---|---|---|
| 4% Polycarbophil | 0.901 ± 0.035 | 2295 ± 170 | Cohesive |
| 4% LV NOCC solution | 1.007 ± 0.107 | 2567 ± 270 | Cohesive |
| 2.5% NOCC(HV) | 1.513 | 3857 | Cohesive |
| 1% NOCC gel | 0.770 ± 0.280 | 1961 ± 410 | Adhesive |
| 2.5% NOCC gel | 0.481 | 1226 | Adhesive |

Notes:
Error limits are one average deviation based on 2–3 determination and values without error limits result from a single measurement.

TABLE 2

Bioadhesion of NOCC Formulations to Cecal Tissue.

| Polymer Sample | Tensile Failure Force (grams) | Force to Separate Tissue (dynes/sq · mm) | Adhesive or Cohesive Failure |
|---|---|---|---|
| 4% Polycarbophil | 1.113 | 2837 | Cohesive |
| 2.5% NOCC (HV) solution | 0.992 ± 0.060 | 2567 ± 140 | Cohesive |
| 1% NOCC gel (1:100) | 0.302 ± 0.010 | 770 ± 30 | Adhesive |
| 1% NOCC gel (1:250) | 0.410 | 1045 | Adhesive |

Notes:
Error limits are one average deviation based on 2–3 determination and values without error limits result from a single measurement.

EXAMPLE 2

This example illustrates the adherent property of an adherent NOCC coating of the present invention.

Six female rats were anaesthetized using sodium pentobarbitol (60 mg/kg) and subsequently sacrificed by cervical dislocation. Twelve femurs were harvested and stripped of connective tissue by sharp dissection. Excess connective tissue was removed from the rat femur by immersing the rat femurs in boiling water for thirty minutes. The femurs were then rinsed and air dried.

Figure 3:
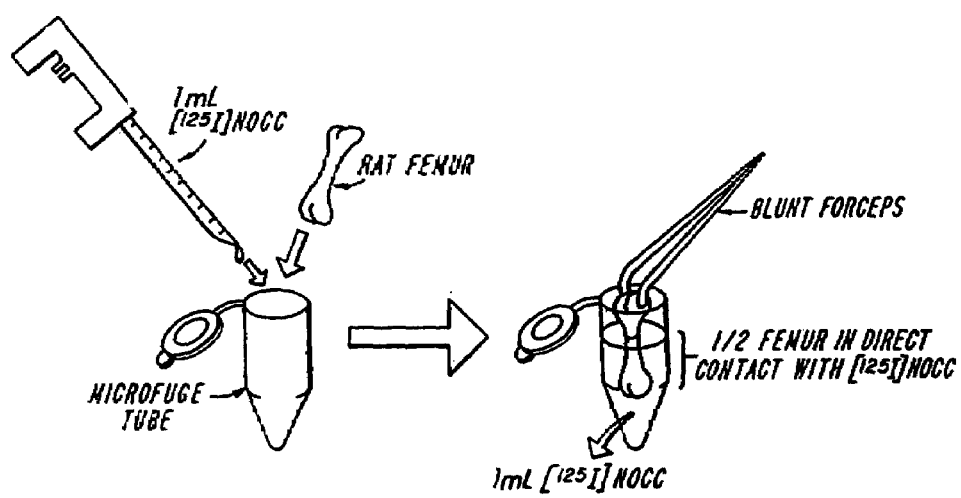
FIG. 3 is a schematic of the procedure used in Example 2.

Each femur was immersed in 1 ml of $^{125}I$ labeled NOCC such that half the surface area of the femur was in direct contact with the $^{125}I$ NOCC solution (FIG. 3). The other half of the femur was used to manipulate the femur. Subsequently, the femur was either placed directly into a scintillation vial and then placed in a γ-counter rack, or the femur was subjected to a uniform "wash" before being placed into a scintillation vial and the γ-counter rack.

Four groups of three $^{125}I$ NOCC treated femurs were subjected to either one wash, two washes, three washes or no washes. A wash consisted of the uniform agitation of the femur in approximately 150 ml of PBS for five seconds. Two washes consisted of a wash, removing the femur from PBS for one second, and then repeating a wash. Hence, three washes consisted of a wash, removal of the femur, a wash, removal of the femur, and one last wash. The PBS solution was replaced for each group of femurs.

Figure 4:
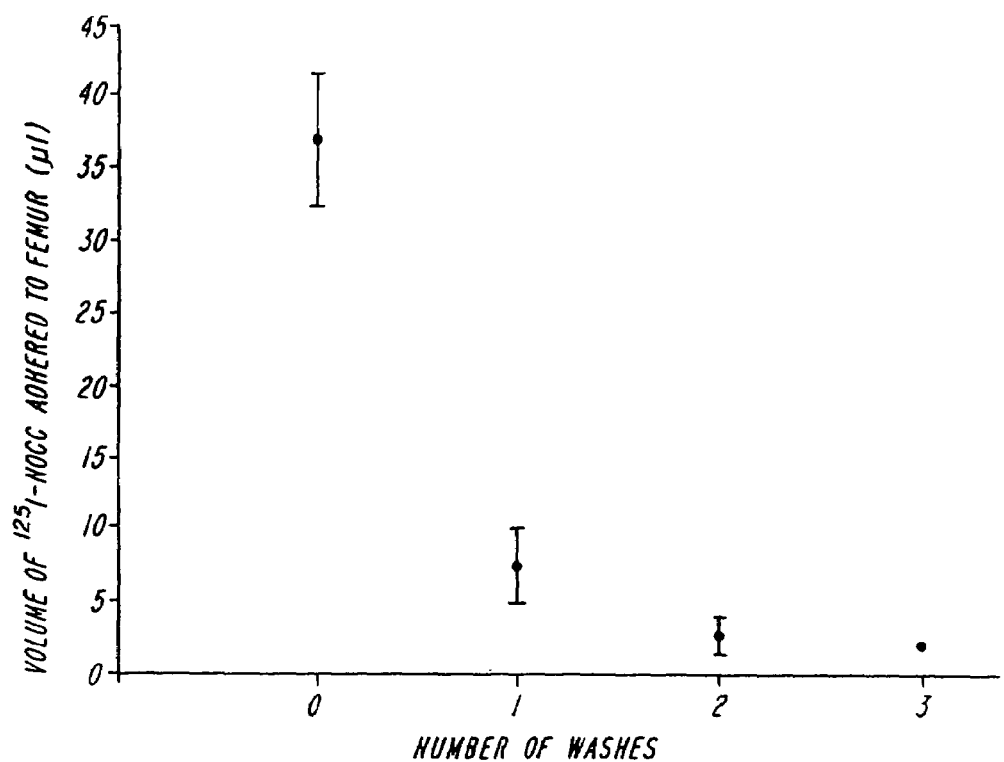
FIG. 4 is graph showing the total volume of $^{125}$I-NOCC adhered to rat femur, as calculated using Equation 1.

The activity of $^{125}I$ NOCC was evaluated by a Beckman γ-counter. The amount of $^{125}I$ NOCC adhered to a rat femur was calculated using Equation 1, which uses the activity of 1 ml of $^{125}I$ NOCC ($7.2\times10^7$ CPM) and the activity of the $^{125}I$ NOCC on the femur, (detected by the γ-counter). The results appear in FIG. 4.

Equation 1:

$$\text{volume of } ^{125}I \text{ NOCC adhered to femur} = \frac{\text{activity}(CPM) \text{ of sample}}{7.2 \times 10^7 CPM} \times 1 \text{ mL}$$

Next, the amount of $^{125}I$ NOCC per unit area of the femur was calculated. The surface area that was in direct contact with the $^{125}I$ NOCC solution was calculated for one representative rat femur.

Equation 2:

$$\text{surface area in direct contact with } ^{125}I \text{ NOCC} = \frac{2\pi rh}{2} + \pi r^2$$

where h=the total height of the femur; r=the radius of the femur

The amount of $^{125}I$ NOCC per unit area of then calculated, using Equation 3, by dividing the surface area of the rat femur in direct contact with $^{125}I$ NOCC into the amount of $^{125}I$ NOCC adhered to the rat femur. The results appear in FIG. 5.

Equation 3:

$$\frac{^{125}I \text{ NOCC per unit area of femur}}{} = \frac{\mu L \text{ of } ^{125}I \text{ NOCC adhered to femur}}{\text{surface area in direct contact with } ^{125}I \text{ NOCC}}$$

The surface area of the rat femur was calculated to be 228 $mm^2$, (radius=2.25 mm and total femur height=30 mm).

Table 3 outlines the number of washes each femur was subjected to, the activity of $^{125}I$ NOCC, amount of $^{125}I$ NOCC adhered to femur, and the amount of $^{125}I$ NOCC per unit area of femur.

TABLE 3

| femur number | Number of washes/femur | activity of $^{125}$I NOCC/femur (CPM) | volume of $^{125}$I NOCC adhered to femur (μL) | volume of $^{125}$I NOCC (μL)/unit area of femur (mm²) |
|---|---|---|---|---|
| 1 | 0 | $2.3 \times 10^6$ | 31.9 | $1.4 \times 10^{-1}$ |
| 2 | 0 | $2.7 \times 10^6$ | 37.5 | $1.6 \times 10^{-1}$ |
| 3 | 0 | $2.9 \times 10^6$ | 40.3 | $1.8 \times 10^{-1}$ |
| 4 | 1 | $6.9 \times 10^5$ | 9.6 | $4.2 \times 10^{-2}$ |
| 5 | 1 | $5.1 \times 10^5$ | 7.1 | $3.1 \times 10^{-2}$ |
| 6 | 1 | $3.9 \times 10^5$ | 5.4 | $2.4 \times 10^{-2}$ |
| 7 | 2 | $1.4 \times 10^5$ | 1.9 | $8.3 \times 10^{-3}$ |
| 8 | 2 | $1.4 \times 10^5$ | 1.9 | $8.3 \times 10^{-3}$ |
| 9 | 2 | $2.9 \times 10^5$ | 4.0 | $1.8 \times 10^{-2}$ |
| 10 | 3 | $1.6 \times 10^5$ | 2.2 | $9.6 \times 10^{-3}$ |
| 11 | 3 | $1.3 \times 10^5$ | 1.8 | $7.9 \times 10^{-3}$ |
| 12 | 3 | $1.8 \times 10^5$ | 2.5 | $11.0 \times 10^{-3}$ |

The results indicate that $^{125}$I NOCC adheres to rat femur. After a third wash, it was found that $9.5 \times 10^{-3}$ +/− 0.002 μL/mm² (or about 0.1 μg NOCC/mm²) of $^{125}$I NOCC remained adhered to the rat femur.

EXAMPLE 3

This example illustrates the effect of adherent NOCC on cellular attachment. In the first assay, 3T3 fibroblasts were maintained in culture in RPMI culture medium supplemented with 10% fetal calf serum (FCS), 20 mM HEPES, 100 U/ml penicillin/streptomycin, 2 mM l-glutamine, and 50 μM 2-mercaptoethanol; referred to as complete RPMI (cRPMI). 3T3 fibroblasts were removed from the stock culture flask by treatment with trypsin, washed and re-suspended to a concentration of $3.0 \times 10^5$ cells/ml in serum free RPMI (sfRPMI; RPMI as before but without the 10% FCS) either alone or with 0.1% NOCC.

These cells were then plated on 96 well Nunclon tissue culture plates which had been pre-coated (overnight, room temperature) with one of four different coating treatments. These were: 1) phosphate buffered saline (PBS) as a control, 2) vitronectin at a concentration of 15 μg/ml in PBS (vitronectin is an ECM protein that fibroblasts adhere to), 3) sfRPMI as a control, and 4) cRPMI, which contains many ECM proteins. After pre-coating, plates were washed three times in PBS to remove the coating media. Cells were plated at a concentration of $3.0 \times 10^4$ cells/well and incubated at 37° C. for 90 minutes. Cells were then observed microscopically, and classed as either adherent or non-adherent based on morphology. Two hundred cells were counted in each well (each coating treatment was done in triplicate), and a mean % adherence±standard deviation (SD) was calculated.

This second assay allows quantification of the effect of adherent NOCC on fibroblast adhesion. In this assay, 3T3 cells were labeled with radioactive chromium ($^{51}$Cr, in the form of Na$_2$$^{51}$CrO$_4$) suspended in sfRPMI, added to the wells of 96-well Nunclon delta plastic plates at a concentration of $2 \times 10^4$ cells/well and allowed to adhere. After a 90 minute incubation at 37° C., a large proportion of fibroblasts will adhere to plastic. Washing of the plate with PBS removed non- or loosely adherent cells. The number of remaining adherent cells was assessed by lysis with 10% sodium dodecyl sulfate (SDS; a detergent) and harvesting the well contents. The lysate was then counted in a gamma counter and disintegrations per minute were recorded. The level of radioactivity from the lysate was compared to that present in $2 \times 10^4$ labeled fibroblasts and is indicative of the number of cells adhering to each well. The adhesion assay was performed in the presence or absence of 0.1% NOCC.

Visual inspection of fibroblast morphology in the presence or absence of NOCC, demonstrated that when fibroblasts were plated in sfRPMI, they consistently displayed an "adherent" morphology; that is, the cells were flattened with complex processes. Regardless of the coating treatment, approximately 80% of cells observed looked like normal cultured fibroblasts. In contrast, when fibroblasts were plated in sfRPMI with 0.1% NOCC, the number of cells displaying the adherent morphology was greatly reduced. In fact, wells pre-coated with PBS or sfRPMI (no ECM proteins present), no cells adhered in the presence of NOCC. When wells were pre-coated with vitronectin or cRPMI, some cells adhered but the adherence was significantly less than that which occurred in the absence of NOCC (FIG. 7).

Hyaluronic acid (HA) was also tested in this system, to determine whether it had similar effects to NOCC. When a similar morphological examination was performed on cells plated in sfRPMI containing 0.1% HA, it was observed that the HA did not have the same effect on fibroblast morphology (FIG. 8).

The $^{51}$Cr adhesion assay was developed to achieve a more quantitative method of measuring fibroblast adherence. The first experiment using the $^{51}$Cr adhesion assay confirmed the results obtained by visual inspection examining the effect of adherent NOCC on adhesion of 3T3 fibroblasts to uncoated Nunclon delta plates. The results confirmed that adherent NOCC blocks adhesion of 3T3 fibroblasts to plastic, by more than 90% using this assay (FIG. 9). This result, taken together with the previous work, suggests that NOCC adheres to the plastic and interferes with the deposition of ECM proteins in a competitive manner.

A competitive assay was performed to test these results with varying concentrations of FCS, which contains the ECM proteins of interest. The $^{51}$Cr adhesion assay was performed using RPMI supplemented with 2%, 5% or 10% FCS as a plating medium (in the presence or absence of 0.1% NOCC). It was found that presence of FCS in the plating medium reversed the inhibitory effect of adherent NOCC on fibroblast adhesion in a dose dependent manner, where 10% FCS fully restored binding of 3T3 to the plates in the presence of adherent NOCC (FIG. 10). There were however, two possible explanations for this effect: 1) adherent NOCC prevents fibroblast adhesion to the ECM proteins which bind to the plate, or 2) adherent NOCC prevents the binding of ECM proteins to the plate in a competitive manner.

To address these possibilities, plates were pre-coated with ECM in the form of RPMI containing varying concentrations of FCS ranging from 2% to 10% overnight at 4° C. The unbound ECM proteins were then washed off. The adhesion assay was performed using these pre-coated plates and cells suspended in sfRPMI in the presence or absence of 0.1% NOCC. The presence of adherent NOCC did not interfere with the adhesion of fibroblasts to the coated plates, thus confirming that adherent NOCC does not inhibit adhesion of fibroblasts to ECM proteins already deposited on the plate (FIG. 11).

To confirm that adherent NOCC competitively interferes with deposition of ECM proteins on plastic surface, plates were pre-coated with NOCC (in sfRPMI) overnight at 4° C., and washed. Fibroblasts suspended in RPMI supplemented with 2%, 5% or 10% FCS were allowed to adhere to such NOCC coated plates or control uncoated plates. In this experiment, the adherence of fibroblasts was determined after 1 hour by measuring the activity of the tritiated thymidine-labelled cells that were attached to the plates. The results (—FIG. 12) showed that fibroblast adherence to NOCC coated plastic is eliminated in the presence of 2, 5 or 10% FCS, supporting the hypothesis that adherent NOCC binds to the plastic plate surface and prevents the deposition of ECM proteins. In the absence of ECM network, fibroblasts are unable to bind to the substrate.

EXAMPLE 4

Figure 13:
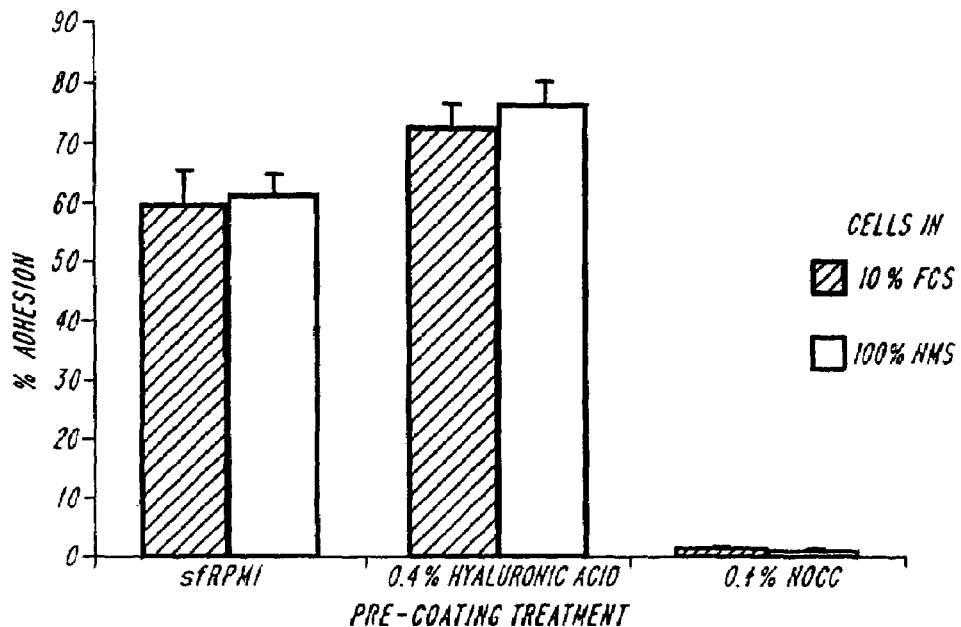
FIG. 13 is a bar graph showing a comparison of adherence by epithielial cells grown in plates that were pre-coated with and without NOCC, as determined by using cells labeled with tritiated thymidine.

In this Example, epithethial cells labeled with tritiated thymidine were used to test whether NOCC could eliminate their attachment to culture plates. Culture plates were pre-coated with NOCC (in sfRPMI) overnight at 4° C., and washed. Labeled epithial cells were suspended in RPMI which was supplemented with FCS and were allowed to adhere to the NOCC coated plates or control uncoated plates. The adherence of the epithelial cells was determined after 1 hour by measuring the activity of the tritiated thymidine-labelled cells following lysis from the plates. The results (shown in FIG. 13) show that the NOCC pre-coating prevents the attachment of epithelial cells

EXAMPLE 5

Figure 14:
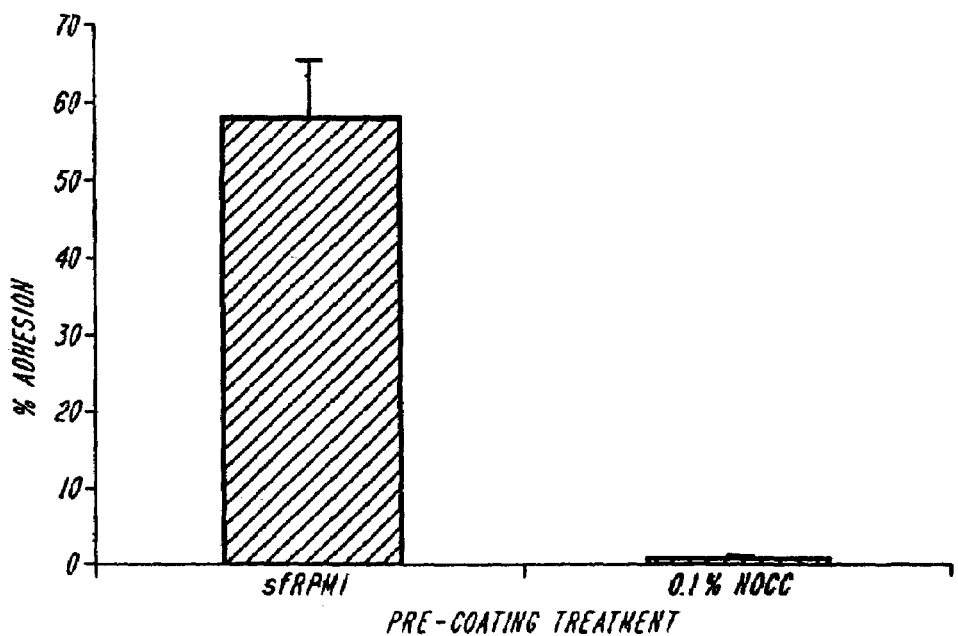
FIG. 14 is a bar graph showing a comparison of adherence by macrophages grown in plates that were pre-coated with and without NOCC, as determined by using cells labeled with tritiated thymidine.

In this Example, an experiment similar to that described in Example 4 was carried out except instead of labeled epitheial cells, tritiated thymidine labeled macrophages (J774M0) were used. Again, the plates were precoated with 0.1% NOCC, and the macrophages were suspended in RPMI and were allowed to adhere to the NOCC coated plates or control uncoated plates. FIG. 14 illustrates that the NOCC precoating inhibits the attachment of the macrophages to the plates.

The foregoing examples are merely exemplary and those skilled in the art will be able to determine other modifications to the described procedures which fall within the scope of the invention. Accordingly, the invention is defined by the following claims and equivalents thereof.

What is claimed is:

1. A method of inhibiting attachment of a protein to a substrate comprising applying an adherent N, O-carboxymethylchitosan coating selected from the group consisting of ionically cross-linked and covalently crosslinked N, O-carboxymethylchitosan to said substrate such that such attachment of said protein is inhibited, and provided that the substrate is not mammalian or non-mammalian cells or tissue wherein adhesion is being inhibited.

2. The method of claim 1, wherein the substrate is selected from medical devices, fermentation units, bioreactors, and solid supports.

3. The method of claim 2, wherein the mammalian tissue is soft tissue.

4. The method of claim 2, wherein the mammalian tissue is hard tissue.

5. The method of claim 2, wherein said medical device is selected from the group consisting of stents, catheters, contact lenses, breast implants, pacemakers and shunts.

6. The method of claim 1, wherein said adherent N,O-carboxymethylchitosan is an adherent solution, hydrogel, paste, particle, bead, pellet, rehydratable film, or sponge.

7. A method of obtaining a population of cells comprising:
 a) supplementing culture media with an adherent N,O-carboxymethylchitosan selected from the group consisting of ionically cross-linked and covalently cross-linked N,O-carboxymethylchitosan;
 b) growing said population of cells in the supplemented media; and
 c) allowing said cells to grow or differentiate,
 wherein proliferation of substrate-dependent cells within said population is inhibited.

8. The method of claim 7, wherein said adherent N,O-carboxymethylchitosan is a solution, hydrogel or paste.

9. The method of claim 7, wherein substrate-dependent cell attachment within said population is inhibited.

* * * * *